United States Patent
Briscoe et al.

(10) Patent No.: US 6,758,809 B2
(45) Date of Patent: Jul. 6, 2004

(54) SURGICAL TOOL FOR ENGAGEMENT OF BODY TISSUE

(75) Inventors: Roderick E. Briscoe, Rogers, MN (US); David J. S. Kim, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 14 days.

(21) Appl. No.: 10/164,734

(22) Filed: Jun. 6, 2002

(65) Prior Publication Data

US 2003/0229271 A1 Dec. 11, 2003

(51) Int. Cl.⁷ .............................................. A61B 17/02
(52) U.S. Cl. ..................................... 600/229; 600/210
(58) Field of Search .................. 600/229, 230, 600/231, 234, 228, 205, 210, 215, 222, 235, 37; 606/1, 191, 207; 248/276.1, 160, 231.51, 230.4, 288.51, 316.5; 269/57, 74, 909; 403/56, 90

(56) References Cited

U.S. PATENT DOCUMENTS

| | | | |
|---|---|---|---|
| 3,096,962 A | * 7/1963 | Meijs .......................... 248/276.1 |
| 4,949,927 A | * 8/1990 | Madocks et al. ............ 248/276 |
| 5,348,259 A | * 9/1994 | Blanco et al. ............... 248/276 |
| 5,513,827 A | * 5/1996 | Michelson ................ 248/279.1 |
| 5,727,569 A |   3/1998 | Benetti et al. ............... 128/898 |
| 5,836,311 A |  11/1998 | Borst et al. .................. 128/897 |
| 5,876,332 A |   3/1999 | Looney ........................ 600/227 |
| 5,899,425 A | * 5/1999 | Corey Jr. et al. ........ 248/276.1 |
| 6,007,486 A |  12/1999 | Hunt et al. .................. 600/205 |
| 6,019,722 A | * 2/2000 | Spence et al. ............... 600/210 |
| 6,019,772 A |   2/2000 | Shefaram et al. ............ 606/159 |
| 6,036,641 A |   3/2000 | Taylor et al. ................ 600/231 |
| 6,113,534 A |   9/2000 | Koros et al. ................. 600/213 |
| 6,152,874 A | * 11/2000 | Looney et al. .............. 600/214 |
| 6,394,951 B1 |   5/2002 | Taylor et al. ................ 600/210 |
| 2001/0025905 A1 | * 10/2001 | Carpenter et al. ........... 248/160 |
| 2001/0037123 A1 | * 11/2001 | Hancock ...................... 606/167 |

FOREIGN PATENT DOCUMENTS

| EP | 0 993 806 A2 | 4/2000 |
|---|---|---|
| WO | WO 01/17437 | 3/2001 |

* cited by examiner

*Primary Examiner*—Kevin Shaver
*Assistant Examiner*—David C. Comstock
(74) *Attorney, Agent, or Firm*—Thomas G. Berry; Daniel W. Latham

(57) ABSTRACT

An improved stabilizer or retractor or other surgical tool having an elongated distal arm carrying a tissue-contacting mechanism at its distal end and a tensioning mechanism at its proximal end for locking functional components of the tool in a desired position or configuration. The tensioning mechanism is mounted to a turret or other structure attaching the distal arm to a base by means of a shorter, proximally extending flexible arm. The flexible proximal arm allows the tensioning mechanism to be moved relative to the base so that it can be placed more conveniently in the operative field.

18 Claims, 3 Drawing Sheets

SURGICAL TOOL FOR ENGAGEMENT OF BODY TISSUE

FIELD OF THE INVENTION

The present invention generally relates to surgery on body tissues and organs. More specifically, the present invention relates to apparatus for engaging body tissue during surgery to position an organ or immobilize tissue subject to motion, such as the heart wall.

BACKGROUND OF THE INVENTION

Coronary artery disease remains the leading cause of morbidity and mortality in Western societies. A number of approaches have been developed for treating coronary artery disease. In less severe cases, it is often sufficient to merely treat the symptoms with pharmaceuticals or to treat the underlying causes of the disease with lifestyle modification. In more severe cases, the coronary blockage can be treated endovascularly using techniques such as balloon angioplasty, atherectomy, laser ablation, stents, and the like. In cases where these approaches have failed or are likely to fail, it is often necessary to perform a coronary artery bypass graft procedure.

The coronary artery bypass graft procedure traditionally required a heart-lung or cardiopulmonary bypass. Due to the risks incurred during cardiopulmonary bypass, beating heart bypass surgery techniques have been developed to allow coronary artery bypass without cardiopulmonary bypass. Several systems are presently available which attempt to immobilize epicardial tissue in the immediate vicinity of an anastomosis site through a pressure stabilizer employing a simple mechanical fork. Such a device stabilizes the heart by pressing a fork downwards onto the heart surface. The fork is typically mounted to an elongated shaft, which in turn is typically mounted to a retractor, holding the patient's ribs apart to create an operative window. Angular movement of the shaft relative to the retractor in some cases is accomplished by means of a turret, which may be clamped in its desired rotational position. Longitudinal movement of the shaft relative to the retractor is typically allowed as well, and clamping mechanisms are typically provided to allow clamping of the shaft to the turret and locking of the fork relative to the shaft. Exemplary pressure stabilization devices are disclosed in U.S. Pat. No. 5,876,332, issued to Looney and U.S. Pat. No. 6,036,641, issued to Taylor, et al., both incorporated herein by reference in their entireties.

Suction stabilization systems, such as the Medtronic Octopus® Tissue Stabilizer (available from Medtronic, Inc., Minneapolis, Minn. USA), instead employ a comparatively long, flexible arm carrying a pair of suction paddles or pods at its distal end. During use, the arm is typically secured to a surgical spreader or retractor, holding the patient's ribs apart to create an operative window. The pods are placed on either side of the anastomosis site and suction is applied to grip and immobilize the surface of the heart. Thereafter, tension is applied along the length of the arm to lock the arm in its position and to lock the position of the pods relative to the arm. Medtronic's device is generally disclosed in pending U.S. patent application Ser. No. 09/396,047, filed by Boone, et al. on Sep. 15, 1999, for a "Method And Apparatus For Temporarily Immobilizing A Local Area Of Tissue, incorporated herein by reference in its entirety. In this device, a single knob, mounted to the proximal end of the arm, is employed to lock the arm in position and additionally to spread the pods somewhat, slightly stretching the heart's surface to provide additional stabilization of the heart surface. In such devices, adjustment of the shaft relative to the surgical retractor is accomplished by varying the configuration of the flexible shaft, prior to locking it in its desired position. Other examples of suction stabilization devices are disclosed in U.S. Pat. No. 6,113,534, issued to Koros, et al., U.S. Pat. No. 6,007,486, issued to Hunt, et al, U.S. Pat. No. 5,836,311, issued to Borst, et al. and U.S. Pat. No. 5,727,569, issued to Benetti, et al., all incorporated herein by reference in their entireties.

In conjunction with stabilization devices, suction retractors are often employed to position the heart to allow access to the desired anastomosis site. The Medtronic Starfish™ device and the Guidant Axius™ Expose™ device are examples of commercially available suction retractors. These devices employ a single, larger suction pod to engage the heart, typically in the vicinity of the heart apex. The suction pod is carried by a flexible arm, which, like the suction stabilizers discussed above, also may be locked into a desired configuration by tension applied along their length. The application of tension to the arm may also serve to lock a carrier for the suction pod relative to the arm to fix the suction pod in a desired orientation relative to the arm, as in the Guidant device. The Medtronic device is described in pending U.S. patent application Ser. No. 09/679,294, filed Jun. 12, 2001 by Keogh, et al. for a "Method and System for Organ Positioning and Stabilization, incorporated herein by reference in its entirety. The Guidant device is described in the brochure "Axius™ Expose™ Device, Instructions for Use, Guidant Corp., 2001, P/N 30462, Rev. A, also incorporated herein by reference in its entirety. Other suction retractors are described in U.S. Pat. No. 6,019,772, issued to Spence, et al. and PCT Publication No. WO 01/17437 by Peng, both also incorporated herein by reference in their entireties.

SUMMARY OF THE INVENTION

The present invention provides an improved stabilizer or retractor, which includes features intended to allow for easier use. These devices are of the type having an elongated arm, hereafter referred to as the distal arm, carrying a tissue-contacting mechanism at its distal end. In preferred embodiments, the devices include a base for mounting the device to a surgical spreader or retractor, carrying a turret coupled to proximal end of the distal arm and allowing rotation of the distal arm relative to the base. The devices in these embodiments also comprise a tensioning mechanism for locking the turret and/or other functional components of the devices in a desired position or configuration. The tensioning mechanism in turn is mounted to the turret or other structure attaching the distal arm to the base by means of a shorter, proximally extending flexible arm, hereafter referred to as the proximal arm.

The tensioning mechanism typically includes a knob, handle or control mechanism of fairly substantial size. The flexible proximal arm allows the tensioning mechanism to be moved relative to the base so that it can be placed more conveniently in the operative field. The inclusion of the proximal arm is believed especially desirable in the context of a device having a turret for positioning the distal arm, as absent this feature, rotation of the turret may sometimes place the distal arm in a desired position at the cost of placement of the tensioning mechanism in an undesirable location. The flexible proximal arm allows the tensioning mechanism to be moved to a more desirable location.

In preferred embodiments, the stabilizer takes the form of a suction stabilizer or retractor having a suction pod or pods mounted to the distal end of a flexible distal arm. In these embodiments, the distal arm is locked into a desired position and configuration by means of the tensioning mechanism. While the invention is most preferably embodied in a suction stabilizer or retractor with a flexible distal arm, certain aspects of the invention may be useful in the context of a pressure stabilizer and/or a stabilizer or retractor with a rigid distal arm.

BRIEF DESCRIPTION OF THE DRAWINGS

The foregoing and other aspects of the present invention will best be appreciated with reference to the detailed description of the invention in conjunction with the accompanying drawings, wherein.

DETAILED DESCRIPTION OF THE PRESENT INVENTION

Figure 1A:
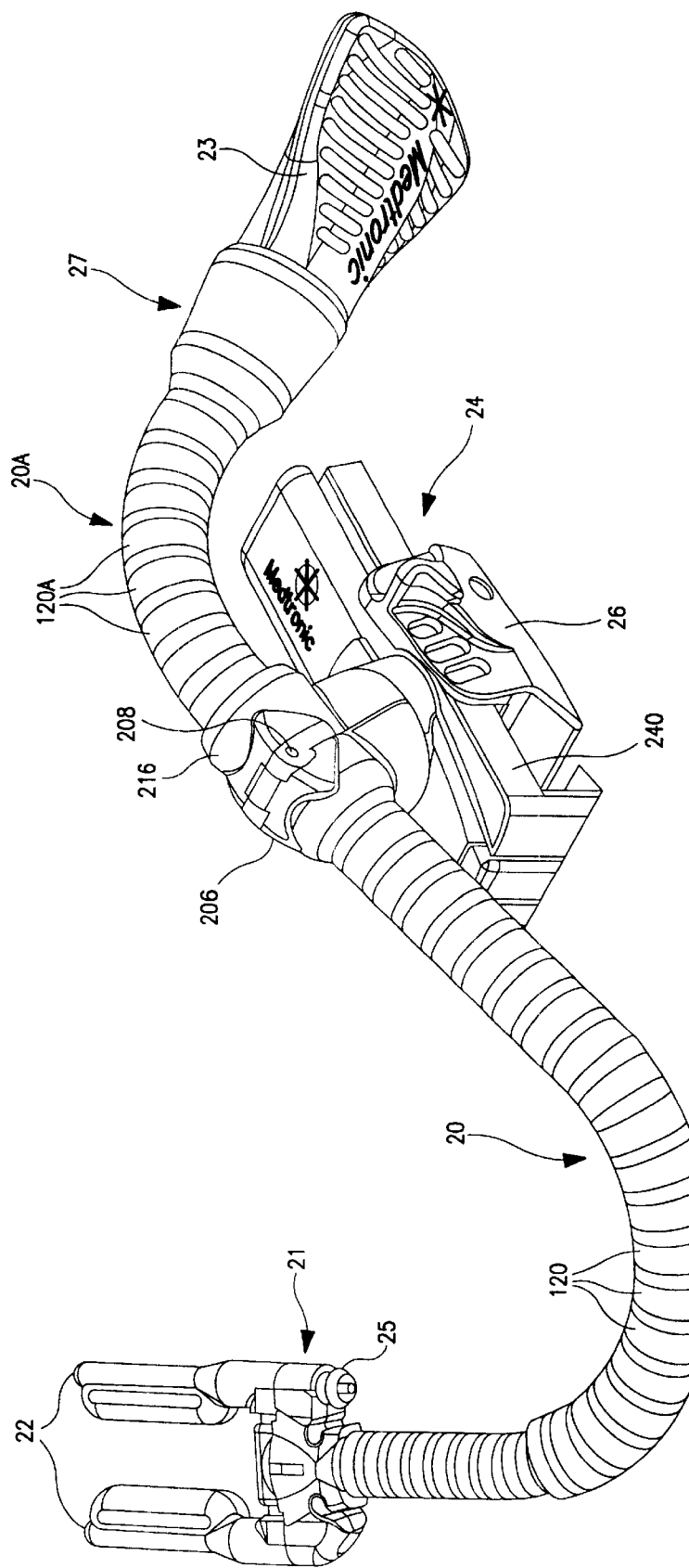
FIG. 1A is a perspective view of a suction stabilizer embodying the present invention.
Figure 1B:
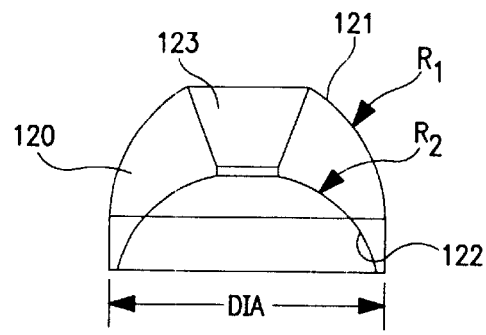
FIG. 1B illustrates a component of the flexible arm of the stabilizer of FIG. 1A.
Figure 1C:
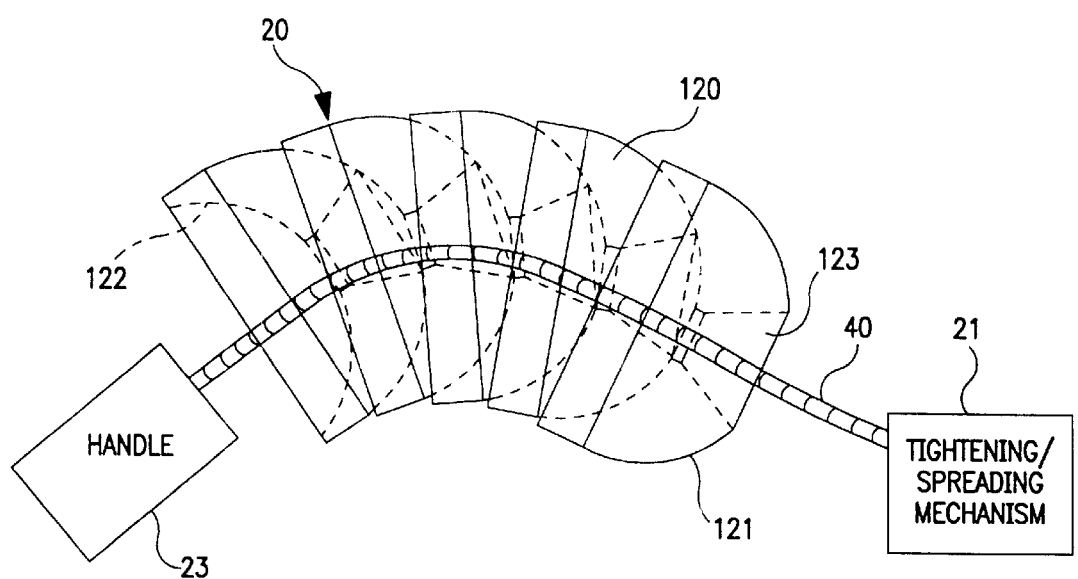
FIG. 1C illustrates the mechanism of operation of the flexible arm of the stabilizer of FIG. 1A.

FIG. 1A is a perspective view of a preferred embodiment of the invention. A flexible, articulating distal arm 20 is attached to base assembly 24 at its proximal end and terminates with tightening/spreading mechanism 21 its distal end. Extending distally beyond tightening/spreading mechanism 21 is a plurality (as shown, two) of suction paddles or pods 22. The suction pods 22 can be connected to a vacuum line by a conventional vacuum line connection 25. Each pod and its suction ports may be constructed in any acceptable manner, such as that used in the Medtronic Octopus™ tissue stabilizer, discussed above. Clamp 26 is designed to attach the entire device to conventional surgical retractors or other equipment located in a fixed relation to the operative site. Articulating distal arm 20 comprises a plurality of "ball and socket" links 120, as illustrated in FIGS. 1B and 1C, discussed below. In some embodiments, the links of distal arm 20 are covered with a thin walled elastomeric sheath, as disclosed in the above cited '047 application. The sheath serves to prevent fragile sutures from catching on the edges where the links join. The sheath is preferably manufactured of silicone rubber, although other materials, such as latex rubber or polyurethane or even collagen, may also be used. The links of the proximal arm may also be covered by a plastic sheath, for example formed of a more rigid thermoplastic, such as a polyurethane.

The proximal end of distal arm 20 is mounted to a turret assembly including two turret members 206 and 216, coupled in a hinging fashion to one another by means of hinge pin 208 these turret members extend around an upwardly extending pivot, mounted to a pivot mount 240, which is part of the base assembly of the device. The turret allows the proximal end of distal arm 20 to be rotated relative to the base assembly 24 and relative to the surgical retractor to which it is typically attached. As discussed in more detail below, the turret members 206 and 216 are clamped in a fixed rotational relationship to the base by means of a tension member passing through the proximal arm 20 and through the turret members, which operates to compress the turret members around the associated pivot extending upward from pivot mount 240. Extending proximally from the turret assembly is a flexible articulating proximal arm 20A, comprising multiple links 120A. The structure of flexible arm 20A may correspond to that of the distal arm 20, and allows for the tensioning mechanism 27 to be moved relative to the base assembly and the retractor to which it is mounted, after rotation of the turret to a desired orientation relative to the base assembly 24. A handle 23 extends from the proximal end of the tensioning mechanism 27 and is operatively coupled to provide tension to the tension member discussed above, which extends from the spreading/tightening mechanism 21, through distal arm 20, through the turret assembly and through the proximal arm 20A. The sheath covering the proximal arm, as discussed below, is coupled to turret member 216 and to the tensinioning mechanism 27 and serves to provide torsional rigidity to the proximal arm.

In this preferred embodiment, application of tension by means of handle 23 serves to perform multiple functions, including locking both the proximal and distal arms 20, 20A in their current configurations, rotationally locking the turret assembly relative to the base assembly 24, and activating the spreading/tightening mechanism 21 to spread pods 22 slightly apart from one another. The details of operation of this mechanism are discussed in more detail in commonly assigned co-pending application Ser. No. 10/122,971 for an "Apparatus for Temporarily Engaging Body Tissue, filed on Apr. 11, 2002 by Goodman, et al., incorporated herein by reference in its entirety.

It should be understood that the present invention may also be practiced in the in the form of a suction retractor, for example corresponding generally to the Medtronic or Guidant suction retractors discussed above or as described in the cited references, with the additional feature of a flexible or articulating proximal arm corresponding to arm 20A, to which the associated tensioning mechanism for the retractor is mounted.

While the preferred embodiment of the invention is practiced in the context of a retractor or stabilizer in which the distal arm is attached to a base assembly by means of a turret, as illustrated in FIG. 1A, it is believed that the invention is also usefully practiced in the context of a device which does not include a turret assembly at the proximal end of the distal arm. Even in such devices, the base assembly is typically movable to multiple locations along the retractor, and the issue of placement of the tensioning mechanism relative to the operative sight may arise in such devices as well.

In addition, while in the preferred embodiment as illustrated, the distal arm takes the form of a flexible articulating arm, the invention is also believed useful in the context of retractors or stabilizers in which the arm is generally rigid, in which the tensioning mechanism would serve to adjust the position of the tissue engaging mechanism at the distal end of the arm and/or to fix a turret assembly at the proximal end of the distal arm relative to a base assembly and/or to operate a spreading/tightening mechanism at the distal end of the distal arm. In these embodiments, as well, the availability of a flexible proximal arm is advantageous for the same reasons as discussed above in conjunction with devices employing flexible, articulating distal arms. Further, while the tensioning mechanism 27 as illustrated in the preferred embodiment of FIG. 1A takes the form of the tensioning mechanism corresponding generally to that employed by the Medtronic devices discussed above, any of the alternative tensioning mechanisms associated with the surgical retractors and stabilizers cited above might usefully be substituted for the tensioning mechanism as illustrated.

FIG. 1B is a cross sectional view of a link used in the distal arm 20 of the embodiment of the present invention illustrated in FIG. 1A. The structure and operation of the links 120A and of the proximal arm 20A may be identical, although they may be of different sizes and/or fabricated of different materials. As seen, each link 120 has a hole 123 that passes through its center. Each link 120 comprises, on its distal end, a spherical protrusion 121; and on its proximal end, a spherical indentation 122. The spherical shapes of adjacent links are nearly identical, such that the links rotate smoothly against one another provided they are not under undue tension with each other.

FIG. 1C is a partial view of a section of the links and tension cable showing the engagement of the cable with the sidewall of the links as the arm is bent. A cable 40 passes through hole of all of the links and is connected between the handle 23 and the tightening/spreading mechanism 21. Rotation of handle 23 tightens the cable and causes the links to hold against each other in place. Immobilization of the links relative to each other during tightening of the cable is facilitated by the shape of the hole 123. As seen, hole is flared, having a larger opening with the surface of the spherical protrusion 121 and a smaller opening through the surface of the spherical indentation 122. The links, as seen in FIG. 1A, may vary in size along the length of the arm, with the links in the most proximal portion of the arm being largest, and the links in the most proximal portion being the smallest. In the preferred embodiment, the links are fabricated out of a highly rigid engineered thermoplastic or of a metal such as stainless steel. The cable is preferably a multi-stranded stainless steel cable, having between approximately 7 to 19 strands. The links and cable may also be manufactured from other materials, including any other suitable metals or highly engineered polymers including any number of available liquid crystal polymers for the links, as well as many other types of cables, including bundle stranded, braided or cabled titanium as well as Kevlar™ for the cable. Some embodiments may also employs a textured surface molded or otherwise formed into the spherical features of the links. When the links are pulled together during tightening, the texturing causes an increase in coefficient of friction between the adjacent spherical surfaces. This has the highly desirable benefit of increasing overall system stiffness. Examples of such surfaces are also disclosed in the above cited '047 application. Tension applied by the cable 40 operates in an identical fashion to lock the configuration of the proximal arm 20A.

Figure 2:
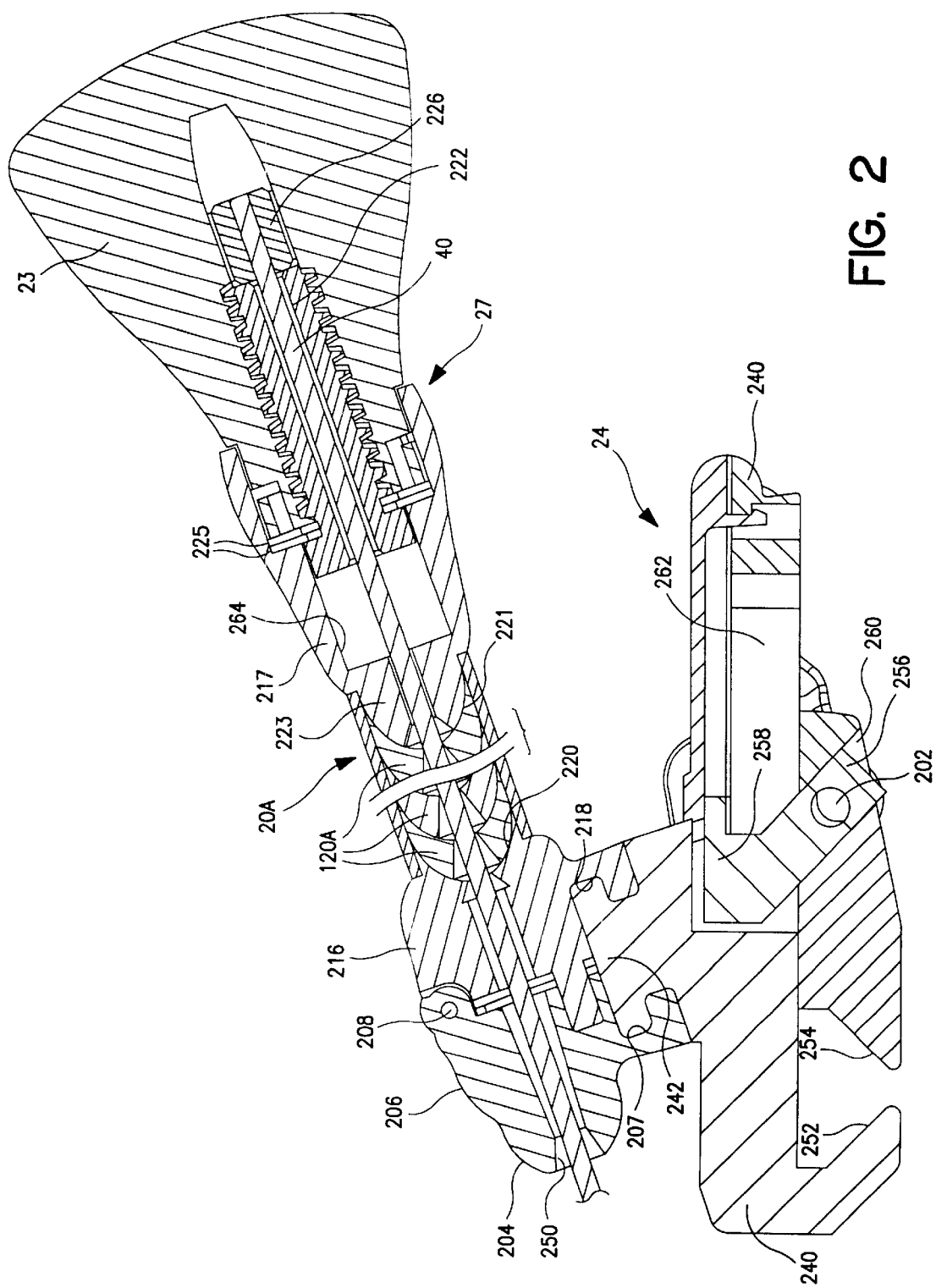
FIG. 2 is a cross-sectional view through the base assembly and tensioning mechanism of the stabilizer illustrated in FIG. 1A.

FIG. 2 is a sectional view through the device illustrated in FIG. 1A, excluding the distal arm. Numbered components correspond to identically numbered components in FIGS. 1A, B and C.

In this view, turret halves 206 and 216 are shown mounted to one another by means of hinge pin 208, and the interrelation of the internal circumferential grooves 207, 218 in turret halves 206 and 216 can be appreciated. These grooves are shown as located closely adjacent to the outer surface of the pivot 242. Movement of the lower portions of the turret halves 206 and 216 toward one another due to tension provided by the cable 40 tightly clamps the turret to the turret pivot 242.

The tensioning mechanism 27 operates as follows. Handle 23 is shown with its threaded inner surface engaging the threaded member 222 and its distal surface lying adjacent washers 225, located in a recess formed in housing 217. The hexagonally shaped distal portion of threaded member 222 is shown lying within a correspondingly configured lumen 264 formed within housing 217, allowing for longitudinal movement of threaded member 222 but not rotational movement. Sleeve 226 is shown located within the handle 26, adjacent the proximal end of threaded member 220 and is mounted to the proximal end of the tension cable 40. Rotation of handle 23 thus causes proximal movement of threaded member 222, applying tension to cable 40.

More clearly visible in this view is the mechanism by which clamp 26 operates in conjunction with the pivot mount 240 to provide a mechanism for attaching the assembly to an associated chest retractor. Pivot mount 240 is provided with a downwardly extending projection having a proximally facing angled surface 252, corresponding to a distally facing angled surface 254 on the distal end of clamp 26. In use, a portion of a retractor is located between these two slanted surfaces, and clamp 26 is moved distally as far as possible so that that portion of the retractor is held between pivot mount 240 and clamp 26. Slanted pin 256 is located within an angled bore 260 formed in clamp 26, having its lower extremity located proximal to its upper extremity. Pin 256 extends through and is located slidably within a downwardly extending slot 262, formed in pivot mount 240. Although not shown in this view, the enlarged head portion 258 of pin 256 bears downwardly along the upper surface 238 of the pivot mount 240. Cam rod 202 has its camming surface located within a cross bore in the pin 256, configured so that rotation of the handle 200 and associated cam rod 202 pulls the pin downward relative to the pivot mount 240 and is correspondingly pulls clamp 26 upward into tight contact with pivot mount 240. Because pin 256 and bore 260 are angled less than 90 degrees relative to the axis along which the clamp 26 slides, rotation of the cam rod 202 by means of an associated lever also causes a slight distal movement of clamp 26 relative to the pivot base 240, tightening it against the associated retractor as well. Cover 241 is shown mounted to the pivot mount 240, covering the slot 262 in which the pin 256 is mounted.

In this view, the construction of the flexible proximal arm 20A can also be appreciated. The links 120A of flexible arm 20A are arranged relative to one another in the same fashion as described above in conjunction with FIGS. 1A and 1B, and correspond generally to the links 120 of the distal arm 20. A plastic sheath 223, for example fabricated of a thermoplastic such as polyurethane, is shown tightly covering the outer surface of links 120A. Sheath 223 overlaps and may be adhesively boded or otherwise attached to turret member 217 and housing 217. Sheath 223 serves to prevent sutures from catching on the edges of the links 120A in the fashion described above. In addition, plastic sheath 223 also provides a mechanism for reducing the tendency of the tensioning mechanism 27 to rotate relative to the base assembly and turret assembly during rotation of knob 23. In alternative embodiments, a tubular metal or plastic braid might be substituted for sheath 223 in order to provide torsional rigidity. On tightening of knob 23, the current configuration of proximal arm 20A is locked in its current configuration in the same way as the configuration of distal arm 20. The distal end of flexible arm 20 nests in a spherical recess 220 formed in the proximal surface of turret member 216. The proximal end of arm 20A is located adjacent a corresponding spherical protrusion 221 on the housing 217 of the tensioning mechanism 27.

While the embodiment as illustrated employs a flexible or articulating proximal arm which is formed of multiple links corresponding generally to those employed in the Medtronic Octopus™ devices, other configurations for the proximal arm can readily be substituted. For example, a set of articulating, interlocking links as employed in the Guidant Axius™ device described above might be substituted. Alternatively, other forms of flexible arms might also be employed, for example corresponding to the flexible arms typically employed in conjunction with adjustable light fixtures, as described in U.S. Pat. No. 6,240,321 issued to Speth, et al, incorporated herein by reference in its entirety or corresponding to the structure of flexible distal arms as described in any of the above cited patents.

Further, while the invention as illustrated employs a flexible plastic sheath to assist in preventing relative rotation of the tensioning assembly relative to the base assembly of the device, other mechanisms for preventing relative rotation of the links might be employed, including interlocking projections and recesses on the links as employed in the Guidant product discussed above. For tensioning mechanisms that do not require rotation of a knob but instead apply tension by means of a lever or the like, a mechanism for preventing rotation of the tensioning mechanism relative to the base might be deleted in its entirety. Further, even in embodiments employing multiple link arms operated by means of a rotated knob, it should be understood that in some such embodiments, compression of the links relative to one another may provide an adequate impediment to relative rotation of the tensioning mechanism and the base assembly, without the necessity of additional measures.

The above specification should be taken as exemplary, rather than limiting, with regard to the claims which follow.

In conjunction with the above specification, we claim:

1. A surgical tool comprising:
   a base;
   a distal arm extending distally from the base and carrying a tissue engaging mechanism;
   a tension member extending through the distal arm;
   a flexible proximal arm, extending proximally from the base and carrying a tensioning mechanism at its proximal end, coupled to apply tension to the tension member, the tension member also extending through the proximal arm,
   whereby the proximal arm may be flexed to permit the tensioning mechanism to be moved relative to the base when tension is not applied to the tension member.

2. A tool as in claim 1, wherein application of tension to the tension member operates to lock the proximal arm in a desired configuration.

3. A tool as in claim 1 or claim 2, wherein the distal arm is a flexible arm and wherein application of tension to the tension member operates to lock the distal arm in a desired configuration.

4. A tool as in claim 1 wherein the distal arm is mounted to a turret, rotatable relative to the base and wherein the proximal arm extends proximally from the turret.

5. A tool as in claim 4, wherein application of tension to the tension member operates to lock the proximal arm in a desired configuration.

6. A tool as in claim 4 or claim 5 wherein application of tension to the tension member operates to lock the turret in a desired orientation relative to the base.

7. A tool as in claim 1 wherein the tissue contacting mechanism is pivotable relative to the arm.

8. A tool as in claim 7, wherein application of tension to the tension member operates to lock the proximal arm in a desired configuration.

9. A tool as in claim 7 or claim 8 wherein application of tension to the tension member operates to lock the tissue contacting mechanism in a desired orientation relative to the base.

10. A tool as in claim 1 wherein the tissue contacting mechanism comprises two tissue contact pods extending from a spreading mechanism.

11. A tool as in claim 10, wherein application of tension to the tension member operates to lock the proximal arm in a desired configuration.

12. A tool as in claim 10 or claim 11 wherein the spreading mechanism is coupled to the tension member and wherein application of tension to the tension member operates to spread the tissue contact pods apart from one another.

13. A surgical tool comprising:
   a base;
   a turret rotatable relative to the base;
   a distal arm mounted to the turret and extending distally from the base and carrying a tissue engaging mechanism;
   a tension member extending through the distal arm;
   a flexible proximal arm comprised of at least one articulating element, the proximal arm extending proximally from the turret and carrying a tensioning mechanism at its proximal end, coupled to apply tension to the tension member, the tension member also extending through the proximal arm,
   whereby the proximal arm may be flexed to permit the tensioning mechanism to be moved relative to the base when tension is not applied to the tension member.

14. A tool as in claim 13, wherein application of tension to the tension member operates to lock the proximal arm in a desired configuration.

15. A tool as in claim 14, wherein the distal arm is a flexible arm and wherein application of tension to the tension member operates to lock the distal arm in a desired configuration.

16. A tool as in claim 13 wherein application of tension to the tension member operates to lock the turret in a desired orientation relative to the base.

17. A tool as in claim 13 wherein the tissue contacting mechanism comprise two tissue contact pods extending from a spreading mechanism.

18. A tool as in claim 17, wherein the spreading mechanism is coupled to the tension member and wherein application of tension to the tension member operates to spread the tissue contact pods apart from one another.

* * * * *